United States Patent [19]

Smith

[11] Patent Number: 5,352,772
[45] Date of Patent: Oct. 4, 1994

[54] 75 KILODALTON INTERLEUKIN-2 RECEPTOR PROTEINS AND THEIR USES

[75] Inventor: Kendall A. Smith, Hanover, N.H.

[73] Assignees: The Trustees of Dartmouth College, Hanover, N.H.; United States of America, Washington, D.C.

[21] Appl. No.: 944,337

[22] Filed: Dec. 19, 1986

[51] Int. Cl.$^5$ .................................... C07K 15/00
[52] U.S. Cl. ............................. 530/350; 530/300; 530/402; 530/413; 530/388.22; 530/389.2; 530/810; 530/811; 530/812; 530/808; 530/351; 530/820; 435/69.1; 435/70.21; 435/70.2; 435/7.1
[58] Field of Search ............... 530/351, 300, 820, 402, 530/350, 413, 810–812; 435/68, 7.1; 424/1.1

[56] References Cited

U.S. PATENT DOCUMENTS

| | | | |
|---|---|---|---|
| 4,411,993 | 10/1983 | Gillis | 435/68 |
| 4,578,335 | 3/1986 | Urdal et al. | 435/68 |
| 4,816,565 | 3/1989 | Hong et al. | 530/351 |

OTHER PUBLICATIONS

Fuji et al., *J. Immunol* 137, 1986, pp. 1552–1556.
Osawa et al. *Eur. J. Immunol.* 14, 1984, 394–376.
Burns et al. *J. Exp. Med.* 161, 1985, pp. 1063–1078.
Tsudo et al. *PNAS* 83, 1986, pp. 9694–9698.
Kuo et al., *J. Immunol.* 137, 1986, pp. 1541–1551.
Leonard et al., *PNAS* 80, 1983, pp. 6959–6961.
Marrack et al., *Scientific American* Feb. 1987, pp. 36–45.
Malek et al., *PNAS* 80, 1983, pp. 5694–5698.
Samelson et al., *PNAS* 80, 1983, pp. 6972–6976.
Robb et al., *J. Exp. Med.,* vol. 154, pp. 1455–1474 (1981).
Leonard et al., *Nature,* vol. 300, pp. 267–269 (1982).
Leonard et al., *Nature,* vol. 311, pp. 626–631 (1984).
Nikaido et al., *Nature,* vol. 311, pp. 632–635 (1984).
Rob et al., *J. of Exp. Med.,* vol. 160, pp. 1126.1146 (1984).
Smith et al., *Proc. Natl. Acad. Sci.,* vol. 82, pp. 864–868 (1985).
Yodoi et al., *J. of Immunology,* vol. 134, pp. 1623–1630.
Greene et al., *J. of Exp. Med.,* vol. 162, pp. 363–368.
Hatakeyama et al., *Nature,* vol. 318, pp. 467–470 (1985).
Sabe et al., *Mol. Biol. Med.,* vol. 2, pp. 379–396 (1986).
Kondo et al., *Nature,* vol. 320, pp. 75–77 (1986).
Sharon et al., *Science,* vol. 234, pp. 859–863 (1986).

*Primary Examiner*—Garnette D. Draper
*Attorney, Agent, or Firm*—Lahive & Cockfield

[57] ABSTRACT

A new cellular protein produced by activated T cells and involved in the high affinity binding of interleukin-2 has been discovered. This protein has a molecular weight of about 75,000 (Mr) and is further characterized as having an affinity for IL-2 (in the absence of other receptor proteins) of about $10^{-9}$ molar and is substantially unreactive with anti-Tac antibodies. This new cellular protein, referred to herein as the "α chain," is believed to interact with the previously isolated 55,000 dalton receptor protein (referred to herein as the "β chain") to form the high affinity interleukin-2 receptor which triggers the growth and mitosis of T cells during an immune response. Methods for isolating and purifying the α chain protein are disclosed herein as well as techniques for cloning and expressing the protein and related materials. Techniques for raising monoclonal antibodies to such proteins are also disclosed. Diagnostic and therapeutic uses for the novel receptor protein (or particular epitopes thereof) as well as monoclonal antibodies (or active fragments) reactive therewith are proposed.

4 Claims, 4 Drawing Sheets

75 KILODALTON INTERLEUKIN-2 RECEPTOR PROTEINS AND THEIR USES

The U.S. Government has rights in this invention pursuant to Grant No. CA-17643 from the National Cancer Institute.

BACKGROUND OF THE INVENTION

The technical field of this invention is interleukin-2 receptors found on T-type lymphocytes (T cells) and, in particular, purified receptor proteins, processes for producing same, monoclonal antibodies having affinity to such proteins, and the use of such proteins and monoclonal antibodies for diagnostic and therapeutic purposes.

Interleukin-2 ("IL-2") is a 15,000 dalton glycoprotein lymphokine which is synthesized and secreted by some T cells following activation with an antigen or mitogen. Interleukin-2 is responsible for activated T cell growth cycle progression and initiates its effects by interacting with specific high-affinity membrane receptors. This interaction is critical to the normal immune response.

In 1982 a monoclonal antibody, termed anti-Tac, was reported by the present inventor and others which specifically bound to the human T cell membrane receptors for interleukin-2. See, Leonard et al., 300 *Nature* 267–269 (November, 1982), herein incorporated by reference, for a discussion of the techniques for preparing monoclonal anti-Tac. The anti-Tac antibody resulted from the immunization of mice with long term cultures of human T cells and was considered to be specific for the interleukin-2 receptor because of its ability to significantly block binding of radiolabeled IL-2 to the HUT-102 cells, a cell line derived from patients with acute T cell leukemia (ATL). The HUT-102 cell line is available from a wide variety of sources and has been used extensively by researchers.

At the same time, a receptor protein, present on normal T cells and a variety of leukemic cells, was identified and at least partially characterized by the present inventor and others. This receptor protein, containing the anti-Tac epitope, was isolated by immunoprecipitation using anti-Tac and found to have a molecular weight of about 55,000–60,000 daltons, as determined by gel electrophoresis. See the above-referenced Leonard et al. paper and U.S. Pat. No. 4,578,335 for further details on this receptor protein.

However, the same experiments that lead to the identification of the 55,000 dalton IL-2 receptor protein also revealed a very large discrepancy between the number of binding sites detectable using radiolabeled IL-2 versus radiolabeled anti-Tac. In particular, ATL cells lines, such as HUT-102, expressed 50–100-fold more anti-Tac binding sites than high-affinity IL-2 receptors. Subsequent experiments appeared to find a second class of sites that bound IL-2 with a 1,000-fold lower affinity (i.e., $Kd=10$ nM versus the high affinity sites with a $Kd=10$ pM). The great majority (greater than 98%) of the IL-2 binding sites found on the surfaces of T cells, especially ATL cell lines, were found to be of the low affinity category.

The confusion concerning the structure of interleukin-2 receptors was further compounded when ATL cell lines and the amino acid sequence of the anti-Tac purified receptor protein were used to identify cDNA clones that encoded the IL-2 receptor. After cDNA transfection experiments revealed solely low affinity IL-2 binding by transformed non T cells, but both high and low affinity IL-2 binding by T cells, it became apparent that an additional, T cell specific protein, was necessary to form high affinity IL-2 receptors. Thus far, investigators have searched for a component that would not of itself bind IL-2, but that would serve to convert the IL-2 binding of the 55,000 dalton Tac protein from low affinity to high affinity.

The structure of IL-2 receptors and their relationship to T cell growth and proliferation is of considerable scientific and clinical importance. T cells play a central role in the induction and regulation of the immune response. In particular, there exists a need to control T cell-induced immune responses in tissue and organ transplanted patients. Existing drug therapies, such as steroid hormones and cyclosporin, are at best indirect agents for immunosuppression. Agents that can block the interleukin-2 ligand-receptor interaction or alter receptor expression, would represent significant new weapons against tissue and organ graft rejection. Similarly, a wide range of autoimmune diseases, such as rheumatoid arthritis and other T cell-driven inflammatory diseases, could benefit from the development of a new class of T cell receptor antagonists. Moreover, a better understanding of the T cell receptor structure may also lead to improved treatments for immunodeficiencies such as those which occur in the acquired immunodeficiency syndrome (AIDS) and neoplastic T cell conditions.

SUMMARY OF THE INVENTION

A new cellular protein produced by activated T cells and involved in the high affinity binding of interleukin-2 has been discovered. This protein has a molecular weight of about 75,000 (Mr), is further characterized as having an affinity for IL-2 (in the absence of other receptor proteins) of about 10 molar and is substantially unreactive with anti-Tac antibodies. This new cellular protein, referred to herein as the "$\alpha$ chain," is believed to associate with the previously isolated 55,000 dalton receptor protein (referred to previously as the Tac antigen and herein as the "$\alpha$ chain") to form authentic high affinity interleukin-2 receptors which trigger the growth and mitosis of T cells during an immune response.

Methods for isolating and purifying the $\alpha$ chain protein are disclosed herein as well as techniques for cloning and expressing the protein and related materials. Techniques for raising monoclonal antibodies to such proteins and assay techniques employing the novel receptor protein (or particular epitopes thereof) as well as monoclonal antibodies (or active fragments) are also disclosed.

In another aspect of the invention, novel therapeutic agents are disclosed which can be useful in treating various immune disorders. One class of such compounds are antagonist compounds, which compete with the high affinity sites on the T cells for IL-2, thereby serving as immunosuppressants. Such antagonist compounds would be particularly useful in combating tissue and organ graft rejection in kidney, liver, heart and other transplants and so-called "graft versus host" disease in bone marrow transplants, without the side effects associated with conventional immunosuppressants. The $\alpha$ chain receptor protein can also be used to prepare IL-2 sequestering agents which essentially remove IL-2 from the blood stream without effecting the T cells directly. Another class of therapeutic compounds are agonist compounds which also react with the IL-2 binding sites on T cells and perform analogous functions to those performed by IL-2 in stimulating T cell growth.

In yet another aspect of the invention, the α chain protein can be useful in designing highly-specific drug deliver systems for T cells to treat immunodeficiencies and other abnormalities. The α chain protein appears to be responsible, at least in part, for receptor-mediated endocytosis whereby IL-2 is internalized by T cells. This feature can be exploited to deliver metabolites, anti-metabolites, anti-viral agents and other therapeutic agents across the cytoplasmic membrane. In such instances, the therapeutic agent can be coupled to a synthetic (or genetically engineered) IL-2 peptide that recognizes and specifically binds to the T cell IL-2 binding sites, such that the conjugate is delivered to the interior of the cell via receptor-mediated endocytosis.

The invention will next be described in connection with certain research results and findings as well as instructions for practicing various aspects of the invention. However, it should be clear that various changes, additions and subtractions can be made by those skilled in the art without departing from the spirit or scope of the invention. For example, various alternative techniques can be employed for raising monoclonal antibodies, purifying receptor proteins, and cloning cDNA to express the alpha chain. None of the cell lines reported herein are unique in their ability to express the alpha chain receptor protein. Although the alpha chain was initially identified on an acute lymphoblastic leukemia (ALL) cell line (the "YT" cell line provided by Dr. Yodoi), subsequent experiments have confirmed the presence of the alpha chain proteins on a wide variety of other T cells of both normal and neoplastic origins. Similarly, the anti-Tac antibodies (provided by Dr. Reinherz) were not unique in their function and the results reported below can be duplicated using other antibodies that recognize the Tac epitope.

DETAILED DESCRIPTION

Cell Cultures

Figure 1:
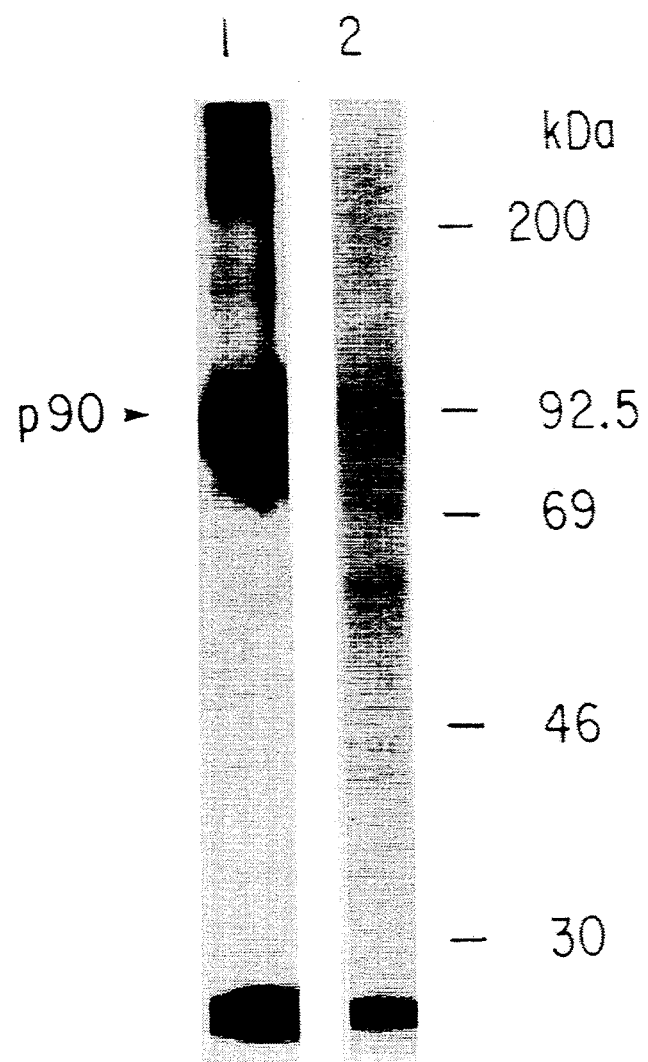
FIG. 1 is a reproduction of autoradiographs obtained by NaDodSO$_4$/polyacrylamide gel electrophoresis of radiolabeled IL-2-binding proteins from an acute lymphoblastoid leukemic (ALL) T cell line clone selected for its lack of Tac epitope expression.

Human leukemic cell lines (YT, JURKAT clone 6.8, HUT-102 and ATL-2) were cultured in RPMI 1640 medium (Gibco Laboratories, Grand Island, N.Y.) supplemented with 10% heat-inactivated FSC (56° C., 30 min, Sterile Systems, Inc., Logan, Utah) 50 U/ml penicillin, 50 μg/ml gentamicin, and 300 μg/ml L-glutamine in a humidified atmosphere of 5% CO$_2$ in air. ATL-conditioned medium was prepared by culturing ATL-2 cells at $3 \times 10^5$ cells/ml for 48 hours. After removing the cells by centrifugation ($1000 \times g$, 10 min), the supernatants were filtered (0.2) pm) and stored at 4° C. prior to use. Individual lots of conditioned medium were standardized by titration with YT cells, and were adjusted so that 20% conditioned medium yielded maximum enhancement of Tac antigen expression within 24 h.

Activated human T cells were prepared by stimulating peripheral blood monoconuclear cells with anti-T3 (Ortho Pharmaceutical Corp., Raritan, N.J.) for 3 days. For some experiments these cells were then cultured for an additional 10 days with 125 pM IL-2. To ensure maximal expression of both high affinity and low affinity IL-2 binding sites by these 13 day synchronized ($G_0/G_1$) cell populations, phorbol 12, 13-dibutyrate (Pdbu, 50 ng/ml, Consolidated Midland Corp., Brewster, N.Y.) was provided during the first 6 hours followed by incubation with IL-2 (125 pM) for 18 hours.

Radiolabeled IL-2 and Anti-Tac Binding Assays

Homogeneous recombinant IL-2 was provided by Takeda Chemical Industries, Ltd., Osaka, Japan, as a 1.0 mg/ml solution in ammonium acetate buffer, pH 5.0. Monoclonal antibodies reactive with the Tac epitope were made available by Dr. Ellis Reinherz (1HT4; IgG$_{2a}$ Dana-Farber Cancer Center, Boston Mass.). IL-2 and anti-Tac ware radioiodinated using lactoperoxidase-glucose oxidase (Enzymobeads, Biorad, Richmond, Calif.) according to the manufacturer's instructions. The specific activity of anti-Tac was $5.3 \times 10^4$ CPM/pmole. Radioiodinated IL-2 was prepared with two difference specific activities ($1.0 \times 10^6$ CPM/pmole and $1.0 \times 10^5$ CPH/pmole) so that binding assays could be carried out at IL-2 concentrations ranging from 1 pM to 100 nM. Binding of both ligands to whole cells was performed, as described in Robb et al., Vol 154 *J. Exp. Med.*, p. 1155 (1981), herein incorporated by reference, except that the radiolabeled ligands were incubated together with the cell suspension ($10^6$ cells in 0.2 ml RPMI 1640 medium supplemented with 10% FCS), overlayed onto a 0.2 ml mixture of 80% silicone oil (Dexter Hysol 550 fluid; Dexter Corp., Orleans, N.Y.) and 20% paraffin oil (0–119; Fischer Scientific Co., Fair Lawn, N.J.). After 20-min incubation at 37° C., the tubes were centrifuged ($8,500 \times g$, 80s), the tips of the tubes containing the cell pellet were severed and the cell-bound and free radioactivity were determined by solid scintillation counting. The calculated values for the number of binding sites per cell were derived by Scatchard analysis of equilibrium binding data after subtraction of nonspecific binding determined in the presence of 150-fold molar excess of unlabeled ligand. The lower limit of detection for both ligands was 50 binding sites/cell.

Flow Cytofluorometry

Cells ($10^6$ cells/ml) were incubated (45 min, 4° C.) with a saturating concentration of anti-Tac (100 nM), washed three times, and then incubated with a 1:20 dilution of fluorescein-conjugated F(Ab')2 fragments of rabbit anti-mouse Ig (Dakopatts; Accurate Chemical and Scientific Corp., Westbury, N.Y.). Samples were passed through an Ortho cytofluorograph (system 50H; Ortho Diagonostic Systems, Inc., Westwood, Mass.) using an argon ion laser at 488 nm excitation wavelength. Green fluorescence was observed using a 630-nm long-pass filter. A minimum of 10,000 cells, gated to exclude nonviable cells, was accumulated for each histogram. All data were analyzed using the Ortho 2150 Data Handler System, and the percentage of positive cells was calculated against a background of nonspecific labeling with normal mouse Ig (1-3%).

cDNA-RNA Hybridization

Total RNA was isolated from cells by solubilization in 4.0 M guanidine hydrochloride, 20 mM sodium acetate (ph 5.0), followed by ultracentrifugation through a 5.7 M cesium chloride cushion. (See Aviv & Leder, Vol. 69, *Proc. Natl. Acad. Sci. USA*, p. 1408 (1972), herein incorporated by reference for further chromatography details.) Poly A+RNA was prepared by oligo-dT affinity column chromatography. Serial twofold dilutions of RNA (10 µg) were applied to nitrocellulose filters (Schleicher and Schuell, Keene, N.H.) using a dot-blot apparatus (Bethesda Research Laboratories, Bethesda, Md.). The filters were baked at reduced pressure for 2h at 80° C. and were pre-hybridized overnight at 42° C. with 6×SSC; 0.15 M sodium chloride, 15 mM sodium citrate, ph 7.0) containing 1% sodium dodecylsulfate (NaDodSO4), poly adenosine (50 µg/ml), sheared salmon sperm DNA (100 µ/ml and 1×Denhardt's solution. Hybridization was effected at 40° C. for 14 h in 50% deionized formamide, X SSC, 0.1% NaDodSO4 with 100 ng 32p-nick-translated probes ($1-2 \times 10^8$ CPM/µg DNA) from Tac cDNA and HLA-B7 cDNA). See Nikaido et al., Vol. 311, *Nature*, p. 631 (1984) and Sood et al., Vol. 78, *Proc. Nat'l. Acad. Sci.*, p616 (1981), herein incorporated by reference, for further details of probe and hybridization techniques.) After high stringency washes with 0.1×SSC, 0.1% NaDodSO4 (30 min, 20° C.; 30 min, 56° C.), radioactivity bound to the filters was detected by autoradiography. Hybridization intensity was quantified by densitometry.

Gel Electrophoresis of IL-2 Binding Proteins

Radioiodinated IL-2 was cross-linked to IL-2-binding proteins according to the following protocol: YT cells ($20 \times 10^6$ cells/ml) were incubated with 10 nM $^{125}$I-IL-2 for 1 h at 4° C., then treated with 1.0 mM disuccinimidyl suberate (DSS) in Hank's balanced salt solution (HBSS). After washing with HBSS, the cells were disrupted using a Dounce homogenizer and the nuclear-free lysate was enriched for plasma membranes. This membrane fraction was solubilized using 1% sodium deoxycholate, 10 mM Tris-HCl (ph 7.4), 0.15 M NaCl, 1 mM phenylmethylsulfonylfuloride, then clarified by centrifugation (100,000×g, 60 min). The supernatant was electrophoresed using a 7.5% acrylamide gel under reducing conditions (20 mM DTT). Similar conditions were employed for normal T cells except that $10 \times 10^6$ cells were exposed to 125I-IL-2 concentrations of 4 nM and 50 pM. After cross-linking with DSS, membrane proteins were solubilized with 0.5% NP-40 prior to electrophoresis under reducing conditions on a 7%-15% acrylamide gradient gel.

For immunoprecipitation of YT cell membrane proteins, the cells were iodinated using lactoperoxidase, then radiolabeled proteins were extracted with a lysis buffer (RIPA) containing 1% Triton X-100. Proteins were precipitated with anti-Tac (100 nM) and formalin-fixed Staphylooccus aureus Cowan I cells, and electrophoresed under reducing conditions on a 7.5% acrylamide gel.

The Effect of ATL Conditioned Medium

YT cells were exposed to ATL conditioned medium for 24 hours after which IL-2 receptor expression was assessed with radiolabeled IL-2 binding assays and anti-Tac immunocytofluorography. ATL conditioned medium promoted a 6-fold increase in Tac antigen expression. By comparison, as displayed by Scatchard plots, the number of high affinity IL-2 receptors was augmented to a similar degree by the ATL-derived conditioned medium (1120 sites/cell to 7880 sites/cell), but the number of IL-2 binding sites with lower affinity remained unchanged (32,200 sites/cell vs. 33,300 sites/cell). The results pointed to the activity contained within ATL conditioned medium as promoting selectively the expression of high affinity IL-2 receptors that also bear the Tac epitope. However, the data also suggested that YT cells express sites with a lower LL-2 binding affinity that do not contain the Tac epitope, and that do not increase upon exposure to ATL conditioned medium.

IL-2 Receptors Expressed by Cell Clones

To define further the types of IL-2 receptors expressed by YT cells, the YT cell line was cloned by limiting dilution (less than 0.3 cell/well. (See Baker et al., Vol. 149, *J. Exp. Med.*, p. 273 (1979) herein incorporated by reference for further description of cloning techniques.) Of 9 clones isolated, 5 resembled the original YT cell line, in that they expressed both high and lower affinity IL-2 binding sites: here, too, the ATL conditioned medium enhanced only the number of high affinity IL-2 receptors. By comparison, 4 of the 9 clones differed from the others, in that no high affinity IL-2 receptor expression could be discerned. Moreover, the lower affinity IL-2 binding sites expressed by these clones contained no Tac epitopes as monitored using either immunocytofluorography or radioiodinated anti-Tac binding. Furthermore, as displayed by the Scatchard plots for a representative clone (2C2), there was no response discernible to ATL-derived conditioned medium monitored by radiolabeled IL-2 binding. Analysis of IL-2 binding to clone 2C2 cells revealed still another perplexing characteristic of these binding sites: the equilibrium dissociation constant (Kd) was found consistently to be $1.5 \pm 0.17$ nM (Mean±SEM, n=9), clearly different from high affinity IL-2 receptors, but also distinguishable from low affinity IL-2 binding sites expressed by normal T cells and ATL cells lines. Normal T cells bind IL-2 with two distinct affinities (Kd=10.6 pM, 1,700 sites/cell; Kd=10.0 nM, 13,000 sites/cell), whereas the YT clone 2C2 cells bind IL-2 with a single intermediate affinity (Kd=1.7 nM, 20,000 sites/cell). Consequently, these data implied that this YT cell IL-2 binding site could be entirely different from the one identified using anti-Tac, especially considering that anti-Tac does not react with the YT-2C2 cells.

A possible explanation for the lack of Tac antigen expression by YT-2C2 cells would be a simple point mutation within the region encoding the Tac epitope. However, in this instance, Tac mRNA should still be detectable. Accordingly, RNA samples from two of the representative YT clones were extracted at intervals before and after exposure to ATL-derived conditioned medium, then hybridized with a probe containing the entire coding sequence for the Tac protein. Using serial dilutions of total RNA (10 ug to 2.5 ug), quantitative analysis of densitometric scans of dot blots proved to correlate directly with the expression of Tac antigen after exposure to ATL conditioned medium. Thus, ATL conditioned medium augmented YT clone 2D7 expression of both detectable Tac mRNA and cell surface Tac antigen, whereas YT clone 2C2 Tac mRNA and Tac antigen expression were undetectable before, and at every interval monitored after exposure to ATL conditioned medium. It is noteworthy that YT clone 2D7 Tac mRNA expression was augmented 10-fold by ATL cell conditioned medium, whereas YT clone 2C2 Tac mRNA expression remained undetectable, identical to that found with RNA from JURKAT clone 6.8, a T-ALL cell line that does not express IL-2 receptors or Tac antigen. Moreover, as shown by the same RNA samples hybridized to a cDNA probe for HLA-B7, equivalent amounts of mRNA from both clone 2D7 and 2C2 were analyzed at each time interval.

To seek further substantiation that YT-2C2 cells do not express Tac mRNA, RNA extracted from clones 2D7, 2F6 and 2C2 was enriched for poly A+ RNA using oligo-dT cellulose, so as to improve the sensitivity of the hybridization assay. Even the 20-fold increase in sensitivity achieved by selecting 4%-5% of the total RNA failed to yield as positive signal when 2C2 poly A+RNA was hybridized with Tac CDNA. By comparison, even in the absence of exposure to ATL conditioned medium, YT clone 2d7 and clone 2F6 both contained easily detectable Tac mRNA, as did HUT-102 cells. Once again, the JURKAT clone 6.8 hybridization was negative and indistinguishable from YT clone 2C2.

Analysis of YT Cell IL-2 Binding Proteins

The only interpretation that explains logically the expression of 20,000–30,000 IL-2 binding sites in the absence of both cell surface Tac antigen and Tac mRNA expression predicts that the gene product responsible for IL-2 binding by these cells should be distinct from the Tac antigen protein. Since YT clone 2C2 cells did not react with anti-Tac, even when immunoprecipitation experiments were attempted, the cell surface proteins reactive with IL-2 were analyzed by forming covalent cross-linkages between $^{125}$I-IL-2 and YT clone 2C2 cells. The results from a representative experiment, displayed in FIG. 1, reveal a single major band migrating at 90,000 (Mr) (p90) as analyzed by autoradiography after NaDodSO$_4$/PAGE (lane 1). When the chemical cross-linking reagent was omitted (lane 2), no cross-linked proteins were discernible. Moreover, although not shown, p90 was also undetectable when a 100-fold excess of unlabeled IL-2 was included in the binding mixture, thus providing the appropriate IL-2 specificity control. Accordingly, the size of the YT clone 2C2 cell membrane protein calculated to be cross-linked to the 15,000 (Mr) IL-2 is 75,000 (Mr) (p75), quite different from Tac antigen, which migrates at 55,000 (Mr)(p55).

Figure 2:
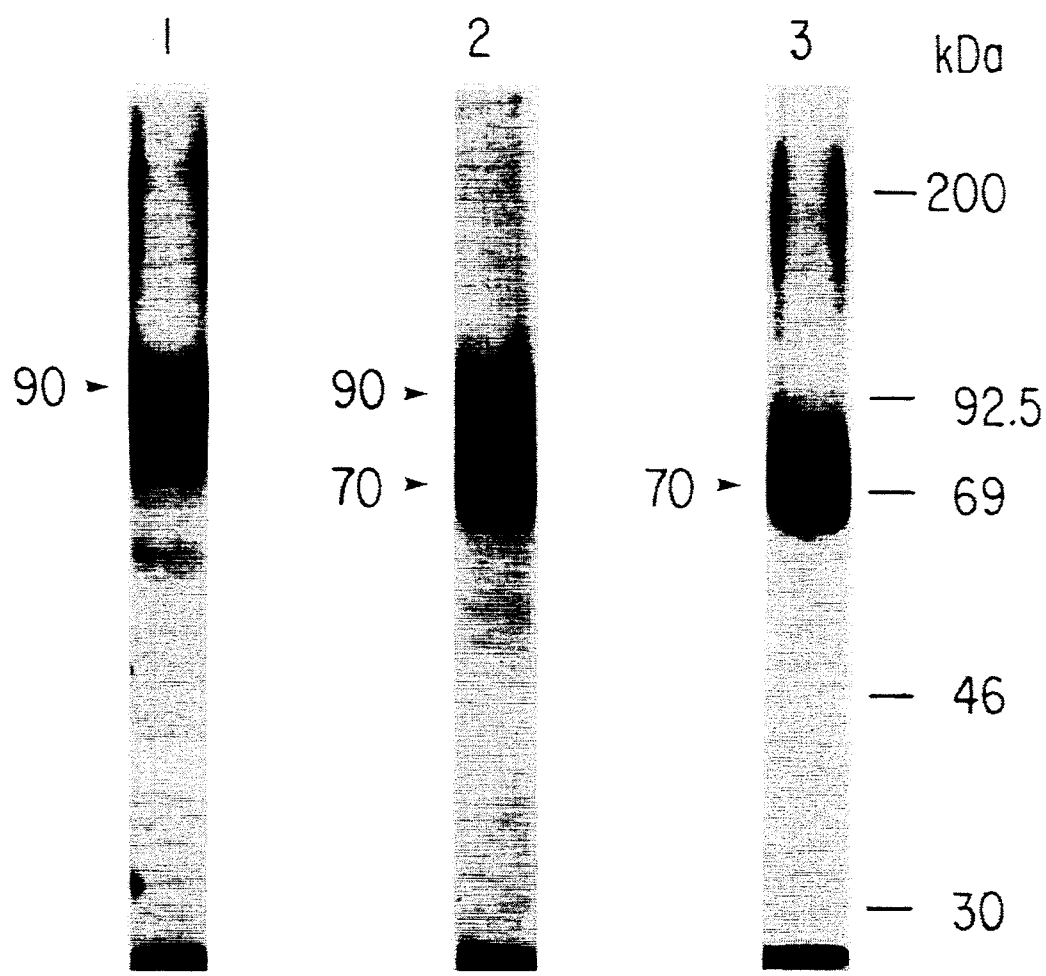
FIG. 2 is a reproduction of autoradiographs obtained by NaDodSO$_4$/polyacrylamide gel electrophoresis of radiolabeled IL-2-binding proteins from acute lymphoblastoid leukemic (ALL) T cells before and after exposure to an ATL conditioning medium and also from an adult T cell leukemic cell line selected for its known expression of the 55,000 (Mr) "β" receptor proteins.

The results obtained with the 2C2 clone indicated that the original YT cells should express at least two cell surface proteins capable of binding IL-2, the p55 Tac antigen and the p75 protein, both of which should be especially evident after augmentation of Tac antigen expression via ATL conditioned medium. Therefore, the original YT cell line was examined for the type of IL-2 binding proteins expressed in the presence and in the absence of exposure to ATL conditioned medium. As shown in FIG. 2, in the absence of exposure to ATL conditioned medium, $^{125}$I-IL-2 is cross-linked predominantly to form a membrane -IL-2 complex indistinguishable from the p90 observed for YT clone 2C2 cells (lane 1). It is noteworthy that $^{125}$I-IL-2 and $^{125}$I-anti-Tac binding assays perform on aliquots of these cells revealed 32,000 intermediate affinity IL-2 binding sites but only 600 high affinity IL-2 receptors and 700 anti-Tac-reactive sites. For comparison, the NaDodSO$_4$/PAGE pattern of YT cells exposed to ATL conditioned medium for 24 hours prior to $^{125}$I-IL-2 binding and cross-linking is shown in lane 2: clearly there are two major bands visible, at 90,000 (Mr) and 70,000 (Mr). Moreover, in contrast to the binding studies performed on the uninduced cells, assays performed on these cells yielded 6000 high affinity IL-2 receptors and 9,800 anti-Tac reactive sites, in addition to 25,400 intermediate affinity IL-2 binding sites.

Figure 3:
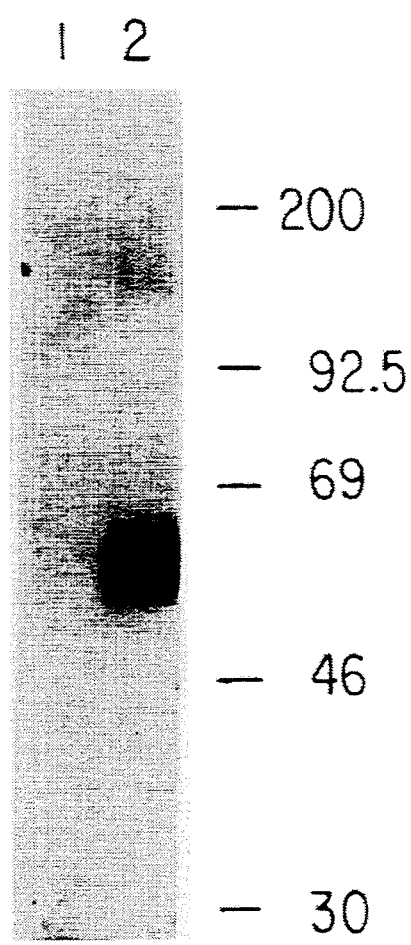
FIG. 3 is a reproduction of autoradiographs obtained by NaDodSO$_4$/polyacrylamide gel electrophoresis of proteins from the same ALL cell line as FIG. 2, comparing the single protein (55,000 (Mr) immunoprecipitated by anti-Tac with the two proteins (55,000 and 75,000 (Mr), respectively) bound and crosslinked to radiolabeled IL-2 in FIG. 2.

Using the same methods, only the 70,000 (Mr) band was detectable after cross-linking $^{125}$I-IL-2 to HUT-102 cells, which express 98%–99% Tac antigen+ low affinity IL-2 binding sites (lane 3). Accordingly, these results are consonant with the interpretation that YT cells are capable of expressing two proteins; one, (p75), does not contain the Tac epitope, whereas the other, (p55), is indistinguishable from Tac antigen as expressed by both normal T cells and ATL cell lines. A final confirmation that YT cells induced by ATL conditioned medium express the typical Tac antigen protein is shown in FIG. 3. The single protein (p55) immunoprecipitated by anti-Tac is in sharp contrast to the two proteins bound and cross-linked to $^{125}$I-IL-2 (FIG. 2, lane 2).

Analysis of Receptors Expressed by Activated Normal T Cells

Figure 4:
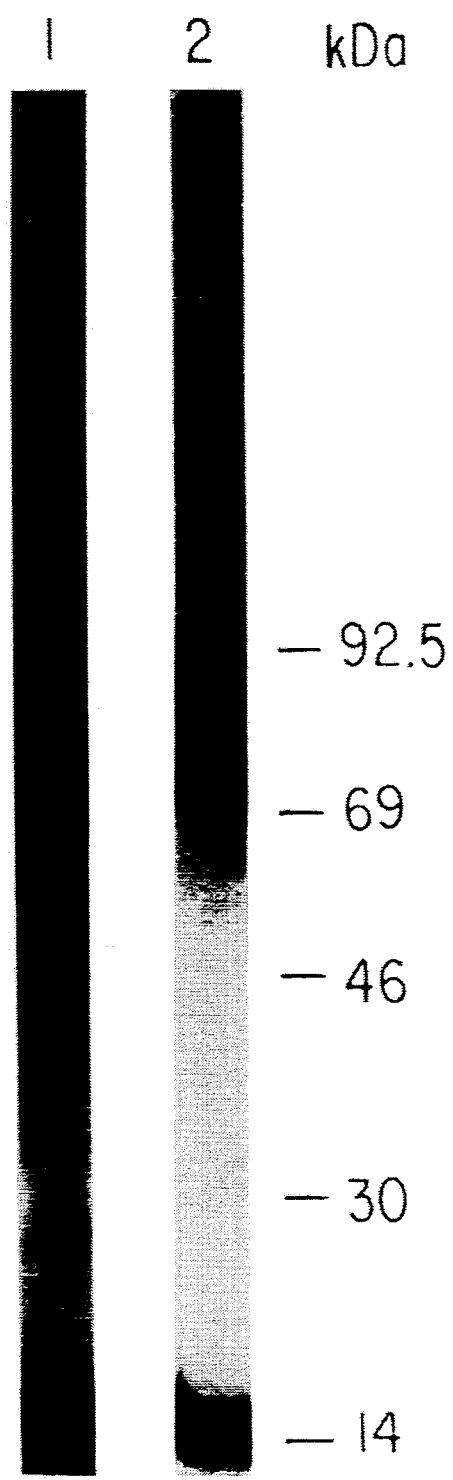
FIG. 4 is a reproduction of autoradiographs obtained by NaDodSO$_4$/polyacrylamide gel electrophresis of radiolabelled IL-2 binding proteins from activated normal human T cells using different radiolabelled IL-2 concentrations.

The correlation of high affinity receptors with the coordinate expression of p55 and p75 implied a fundamental finding: both IL-2 proteins may be essential for the formation of functional, high affinity receptors. If so, then normal activated T cells should also co-express p55 and p75. To assess this possibility, $G_0/G_1$-synchronized normal human T cells were activated by phorbol dibutyrate, and cultured with IL-2 for 18 hours, since previous studies had established that this activation protocol results in a ratio of 10:1 low affinity to high affinity IL-2 binding sites. To reveal p75, which was anticipated to be expressed in limited amounts compared with the easily detectable amounts of p55, two different $^{125}$I-IL-2 concentrations were used for binding prior to cross-linking: a high IL-2 concentration calculated to saturate a majority of the low affinity binding sites, and a low IL-2 concentration that would saturate only a few low affinity finding sites but all of the high affinity receptors. The results, shown in FIG. 4, are entirely consistent with those already found for YT cells, and substantiate that high affinity binding correlates with IL-2 binding to both p75 and p55. Accordingly, as shown in lane 1, when low affinity binding predominated, only one $^{125}$I-IL-2 cross-linked protein is visible at 70,000 (Mr). In contrast, at a low $^{125}$I-IL-2 concentration (lane 2), which favors the proportion of high affinity receptors relative to low affinity binding sites occupied, two bands emerge distinctly (Mr 70,000 and 90,000).

The discovery of another IL-2 binding protein, and the evidence that Tac antigen and this new IL-2 binding protein are co-expressed by cells that have detectable high affinity receptors, now makes essential an entirely new conceptual formulation of the structural basis for functional, high affinity IL-2 receptors.

The conclusion appears inevitable and incontrovertable that both of these IL-2 binding proteins must be important for the formation of high affinity IL-2 receptors. In this respect, the stoichiometry of $\beta$ chain expression as monitored by anti-Tac and the expression of high affinity receptors by YT cells stimulated with ATL conditioned medium is especially convincing. Moreover, this interpretation is even more compelling when it is appreciated that either chain expressed separately makes solely for lower affinity IL-2 binding sites.

The size of the IL-2R $\alpha$ chain, being 75,000 (Mr), rather than only 55,000 (Mr), provides for the expectation that the cytoplasmic domain of the $\alpha$ chain will be larger than the rather short 13 residues of the $\beta$ chain, and thus yield some insight on possible pathways activated by IL-2 receptors. If the $\alpha$ chain contains all the structures necessary for signal transduction, cells expressing only the $\alpha$ chain, exemplified by the YT clone 2C2 cells, should respond to IL-2. Thus far, we have yet to detect IL-2-mediated signal transduction via the YT-2C2 $\alpha$ chain, but these cells are neoplastic and are capable of proliferating without IL-2. It remains a distinct possibility that both $\alpha$ and $\beta$ chains are required for detectable signal transduction.

The functional role of the $\alpha$ chain also requires reconsideration in the light of these new findings. In earlier experiments, we found that IL-2 itself induced the expression of the $\beta$ chain, and others found this induction to result from enhanced transcription. The IL-2 mediated transcriptional activation becomes manifest ultimately as a 10-fold increase in the cell surface density of Tac antigen+ low affinity IL-2 binding sites. Concomitantly, high affinity IL-2 receptors decline by as much as 50% in the presence of IL-2. Our own metabolic studies have traced the disappearance of the high affinity IL-2 receptors to IL-2-mediated accelerated internalization of ligand-receptor complexes. Accordingly, these observations are in harmony with the interpretation that the $\alpha$ chain contains the structural information necessary for ligand-mediated internalization, whereas the $\beta$ chain does not. Consistent with this view, our previous studies found a very slow turnover of Tac antigen in comparison with high affinity IL-2 receptors. Therefore, IL-2 binding to high affinity receptors promotes rapid internalization of $\alpha$ chains (and perhaps associated $\beta$ chains), while simultaneously, signals are generated that result ultimately in enhanced expression of $\beta$ chain mRNA and low affinity cell surface binding sites.

Although the present studies indicate that $\alpha$ chains and $\beta$ chains are expressed together on the cell surface, it is not clear how these two chains associate with one another. However, it is likely that the $\alpha$ and $\beta$ chains are linked physically, considering the effect of anti-Tac: even though the Tac epitope is expressed only on the $\beta$ chain, anti-Tac prevents IL-2 binding both to low affinity sites and to high affinity receptors. In this regard, we have recently completed an extensive study of $\beta$ chains under both non-reducing and reducing conditions, and have found that these chains form preferentially disulfide-linked homodimers capable of binding two IL-2 molecules. In contrast, $\alpha$ chains expressed in the absence of $\beta$ chains by YT clone 2C2 cells do not form homodimers. The behavior of these IL-2-binding proteins, especially the homodimer formation by $\beta$ chains, is reminiscent of the behavior of the T6 and T8 glycoproteins, which are structurally homologous members of the immunoglobulin family. On immature thymocytes T8 is found disulfide-linked to T6, whereas T8 homodimers are expressed by mature T cells, which lack T6 molecules. Thus, like the immunoglobulin family, whose members preferentially associate with themselves, or other members of the same group (e.g., Ig heavy and light chains), the $\alpha$ and $\beta$ chains of the IL-2 receptor may well prove to associate with one another as members of a family of homologous, but separate and distinct lymphokine receptor molecules.

Since $\alpha$ chains and $\beta$ chains bind IL-2 with distinctly different affinities (Kd = 1 nM and 10 nM, respectively), the question arises whether the same or different sites on the IL-2 molecule interact with each binding protein. If the same configuration of the IL-2 molecule were responsible for binding to both chains, one would anticipate some measure of competition between the two binding proteins, which would be evident as negative cooperation in the analysis of IL-2 binding curves. Actually, quite the opposite occurs, i.e., the expression of both proteins is required for high affinity IL-2 binding, thereby pointing to two distinct active sites on the IL-2 molecule responsible for interacting separately with each chain. This interpretation is particularly persuasive, as it hints that high affinity IL-2 binding sites are formed from the combination of the $\alpha$ and $\beta$ chains in a manner similar to the formation of the antigen binding site from residues contributed by both the heavy and light chains of immunoblobulin. Particularly convincing in this regard is the finding that the chain present in limiting amounts dictates the number of high affinity receptors, and either $\alpha$ or $\beta$ chains can function in this role. For example, normal activated T cells and ATL cell lines display excess $\beta$ chains as evidenced by the $^{125}$I-IL-2 cross-linking experiments, and consequently the number of high affinity receptors depends upon the absolute number of $\alpha$ chains expressed. In contrast, YT cells express $\alpha$ chains in excess, and high affinity receptors are detected only when the cells are induced to express $\beta$ chains.

Since the $\beta$ chain of the IL-2 receptor appears to have a much wider tissue distribution than do high affinity IL-2 receptors, it is likely that the simultaneous expression of $\alpha$ chains and $\beta$ chains is rigorously restricted to T cells stimulated via the T cell antigen receptor complex. Moreover, as IL-2 itself causes such a marked induction of $\beta$ chain expression, it is possible that the $\alpha$ chain gene expression is triggered solely via the T cell antigen receptor complex whereas $\beta$ chain expression is regulated by the IL-2-$\alpha$ chain interaction. Such a model predicts that during the T cell proliferative response to antigen, IL-2 receptor $\alpha$ chains are expressed prior to $\beta$ chains. A sequential activation of $\alpha$ chains followed by $\beta$ chains is attractive, in that the IL-2-$\alpha$ chain-mediated induction of $\beta$ chains would have the effect of promoting formation of the more biologically efficient high affinity receptors, thereby lowering by 100-fold the IL-2 concentration required for binding and receptor activation.

The phenotype of the YT cells, particularly of the 2C2 clone, deserves comment, as it may well be of importance for the biologic relevance of the L-2 R α chain. The YT cells resemble "double negative", very immature (class I) thymocytes, in that analysis by immunocytofluorometry using T cell-specific monoclonal antibodies results consistently in the following pattern: $T3^-$, $T4^-$, $T6^-$, $T8^-$, $T9^+$, $T11^+$. Consequently, the expression of these newly recognized IL-2 binding sites by leukemic cells that resemble normal, immature, class I thymocytes, may well be a clue that this binding site could play some role in normal thymocyte proliferation or differentiation. In addition, the 2C2 clone even lacks expression of T11, the sheep erythrocyte receptor, which recently has been proposed as an activation structure and the binding site for a newly recognized 12,500 (Mr) lymphokine produced by $T4^+$ cells. Since YT 2C2 cells are $T^{11-}$ and do not respond to the activity contained within ATL conditioned medium, ATL-derived activity and the lymphokine activity produced by normal $T4^+$ cells may yet be attributable to the same molecule(s).

It is particularly noteworthy that many other polypeptide hormone receptors are known to be present in both high affinity and low affinity forms, yet no structural explanations for these distinct receptor classes have been uncovered. Consequently, it is likely that the proposed model system, which involves the generation of high affinity IL-2 receptors via an interaction between two distinct low affinity binding proteins, will be found to reflect a general aspect of hormone-receptor systems. For studies relating to T cell proliferation, the discovery of the IL-2 receptor α chain is particularly timely, in that all attempts thus far to attribute functional, high affinity IL-2 receptors to the Tac protein alone have been futile.

Monoclonal Antibodies To The α Chain Protein

Monoclonal antibodies to the α chain receptor protein or active fragments of such antibodies can be generated by applying generally known cell fusion techniques (cf. G. Kohler, C. Milstein, Vol. 6, *Eur. J. Immunol.*, pp. 511–519 (1976) and M. Shulman et al., Vol. 276, *Nature*, pp. 269–270 (1978) herein incorporated by reference) to obtain a hybridoma producing the antibody, by deriving a monoclonal antibody from the hybridoma, and (optionally) by subjecting the monoclonal antibody to proteolysis to obtain the active Fab fragment.

Monoclonal antibodies are prepared by obtaining mammalian lymphocytes (preferably spleen cells), committing the lymphocytes to produce antibodies (e.g., by immunizing the mammal with the particular antigenic determinant of interest beforehand), fusing the lymphocytes with myeloma (or other immortal) cells to form hybrid cells, and then culturing a selected hybrid cell colony in vivo or in vitro to yield antibodies which are identical in structure and specificity.

In particular, monoclonal antibodies to the α chain receptor protein can be raised by employing whole cells (from a cell line such as YT clone 2C2, a cell line which predominantly expresses the α chain) as an antigen. Mice or other animals can be challenged by injection with a solution of such whole cells emulsified in complete Freund's adjuvant at weekly intervals. After the initial injection, the booster injections can be administered without adjuvant or emulsified in incomplete Freund's adjuvant. Alternatively, synthetic peptides or fragments of the α chain protein produced by genetically transfected cells (see discussion below) can be used as immunogens.

Serum samples from the immunized animal can be taken and analyzed by an enzyme linked immunoabsorbent ("ELISA") assay or the like for antibody reaction with the immunization agent. Animals that exhibit antibodies titers are sacrificed and their spleens homogenized. Alternatively, the spleen cells can be extracted and the antibody-secreting cells expanded in vitro by culturing with a nutrient medium. The spleen cells are then fused with myeloma (or other immortal) cells by the above-referenced procedure of Kohler and Milstein. The hybridomas so produced are screened (i.e., cloned by the limiting dilution procedure of the above-referenced Baker et al. article) to select a cell line producing antibodies which react with human α chain receptor proteins. Large scale antibody production can be obtained from such anti-α chain producing cell lines by various techniques, including the induction of ascites tumors (e.g., after priming with pristane) and the purification of such antibodies from the ascites fluid by Protein A-Sepharose affinity chromotography.

For a further description of general hybridoma production methods, see Oi and Herzenberg, "Immunoglobulin-Producing Hybrid Cell Lines" in *Selected Methods in Cellular Immunology* (Mishell and Shiigi, Ed., W. H. Freeman & Co., 1980) and Scearce and Eisenbarth, "Production of Monoclonal Antibodies . . ." in Vol. 103 *Methods In Enzymology*, pp. 459–469 (1983), and U.S. Pat. No. 4,411,933 issued to Gillis on Oct. 25, 1986, herein incorporated by reference. Human antibodies (i.e., those obtained from human-human or human-animal hybridoma) can be used as well as animal antibodies. For descriptions of human hybridoma production techniques, see U.S. Pat. No. 4,451,570 issued to Royston et al. on May 29, 1984; U.S. Pat. No. 4,529,694 issued to Lazarus et al. on Jul. 16, 1985 and Zurawski et al., "Continuously Proliferating Human Cell Lines Synthesizing Antibody of Predetermining Specificity" in *Monoclonal Antibodies* (Plenum Press, New York 1980), also incorporated by reference.

Active fragments can be derived from the monoclonal antibodies disclosed herein by a number of techniques. For example, purified monoclonal antibodies can be cleaved with an enzyme, such as pepsin and subjected to HPLC gel filtration. The appropriate fraction containing Fab can then be collected and concentrated by membrane filtration or the like. For further description of general techniques for the isolation of active fragments, see for example, Khaw, BA et al., Vo. 23 *J. Nucl. Med.*, pp. 1011–1019 (1982), incorporated by reference.

The antibodies and fragments used herein can be labeled preferably with radioactive labels, by a variety of techniques other than the above-described Baker et al. technique. For example, the biologically active molecules can also be labeled with a radionucleatide via conjugation with the cyclic anhydride of diethylenetriamine penta-acetic acid (DTPA) or bromoacetyl aminobenzyl ethylamine diamine tetra-acidic acid (BABE). See Hnatowich et al., Vol. 220 *Science,* pp. 613–615 (1983) and Meares et al. Vol. 142 Analytical Biochemistry, pp. 68–78 (1984) incorporated by reference for further description of labeling techniques.

Cloning and Expression of cDNA for the Alpha Chain Protein and Epitopes Thereon Probes can be constructed using conventional techniques to identify the DNA coding for the α chain IL-2 receptor protein. Such probes comprise a group of nucleotide sequences which encode a portion of the amino acid sequence of the α chain protein. Pools of such probes enable isolation of a DNA encoding the intact protein.

For example, total cellular RNA can be isolated from cells known to express the protein by extraction. An oligo-dT-cellulose column can then separate mRNA. In addition, the mRNA can be size fractionated by, for example, agarose gel electrophoresis. The fraction which includes the mRNA of interest may be identified by inducing transient expression in a suitable host cell and testing for the presence of α chain protein using, for example, IL-2 itself or antibodies as described above employed in an immunoassay. The mRNA fraction of interest is then copied into single stranded cDNA using reverse transcriptase. The second complementary strand of DNA is then synthesized from the first using DNA polymerase I. The resulting double stranded DNA is then ligated into vectors which are used to transfect bacterial hosts to produce a cDNA library. Radiolabeled synthetic deoxyoligonucleotide probes complementary to the DNA encoding known partial amino acid sequences of the α chain protein are then used to identify the DNA which encodes the protein. The complete amino acid sequence can then be predicted from the DNA sequence and the appropriate bacterial clone can be further cultured for large scale production of the protein.

More specifically, the α chain protein can be purified from T cell extracts by any of a number of known biochemical fractionation techniques, such as gel filtration, ion exchange chromatograph, high pressure liquid chromatography or the like. The appropriate fraction from the gel or chromatography column is identified by assaying aliquots from each fraction by a soluble receptor binding assay employing radiolabeled IL-2 in a manner similar to the radioassays described above. Alternatively, or as an additional purification step, affinity chromatography can be employed using a solid phase IL-2 column (e.g., interleukin-2 bound to microbeads) or an antibody column (e.g., with monoclonal antibodies prepared as described above, bound to a solid support) to obtain purified α chain receptor proteins.

The purified protein is then analyzed to obtain the amino acid sequence (i.e., preferably about 10-35 amino acid residues) of the amino terminal portion of the molecule. Samples of homogeneous α chain protein, as isolated above, can be analyzed for amino acid composition and sequence using an automated sequencer (Applied Biosystems, Beckman or equivalent protein sequencer) employing the Edman degradation or similar techniques. See generally Konigsberg et al., "Strategy and Methods of Sequence Analysis" and Niall, H., "Automated Methods for Sequence Analysis," Vol. 3, *The Proteins*, pp. 1-178 and 279-238, respectively, (1977), herein incorporated by reference for further description of amino acid sequencing techniques.

The amino acid sequence from the purified protein is then used to construct a radiolabeled synthetic deoxyoligonucleotide probe complementary to a portion of the amino acid sequence. Such oligonucleotides are constructed from radiolabeled nucleotides by protecting one end of the first nucleotide with a blocking group and condensing this precursor with a nucleotide which is blocked at the other end. One of the blocking groups is then removed and the process of condensation, removal of one or the other blocking groups, and recondensation is repeated until an oligonucleotide of the desired length is obtained. See generally, Gail et al., "Rapid Synthesis of Oligodeoxyribonucleotides: A New Solid-Phase Method," vol. 4, *Nuc. Acids Res.*, pp. 1135-1158 (1977), herein incorporated by reference, for further details of oligonucleotide synthesis.

In the next step, a cDNA library is constructed by extracting the cytoplasmic RNA from a cell line known to express the α chain protein and fractionating the extract by gel electrophoresis or the like to isolate that portion of the heterogeneously sized mRNA believed to contain the transcription instructions for the α chain protein. Proper fraction selection can be confirmed by expression in a transient expression vehicle such as frog oocyte cells. Oocytes expressing the α chain can be detected by binding assays using radiolabeled IL-2, or alternatively, by binding using radiolabeled antibodies reactive with the α chain. The appropriate mRNA fraction selected is copied to single stranded cDNA using reverse transcriptase, and the second cDNA strand is then synthesized by DNA polymerase I. The cloned, double-stranded cDNA is introduced into plasmid vectors which are then transfected into appropriate bacterial hosts, such as *E. coli*. The entire collection of cDNA clones can be separated from each other by limiting dilution techniques to form a collection of bacterial colonies which comprise the cDNA library. See Maniatis, *Molecular Cloning*, pp. 188-246 (1982), herein incorporated by reference, for further details of mRNA extraction and cDNA cloning.

Portions of the individual bacterial colonies that comprise the cDNA library are then transferred onto filter paper and lysed; the filter is then washed to remove intracellular debris and the DNA is fixed to the filter by baking. The immobilized DNA is then treated with the radiolabeled oligonucleotide probe, prepared as described above. If DNA complementary to the probe is present in a particular colony, the probe will hybridize to it, thus rendering it detectable by autoradiography. The particular colony can then be further cultured and its DNA extracted therefrom to isolate the α chain gene. From this gene, the DNA sequence (and, consequently, the full corresponding amino acid sequence) can be determined by the Maxam-Gilbert technique or related procedures. See, Maxam & Gilbert, Vol. 65, *Methods in Enzymology*, pp. 479-559 (1980), herein incorporated by reference, for further details of DNA sequencing.

The plasmid containing the α chain gene can also be further transfected into other cell lines for expression or large scale production. Moreover, the gene can be modified to produce analog proteins or fragments (e.g., the surface amino acid residues) that retain the epitopic features of the α chain receptor protein. See generally, Old and Primrose, *Principles Of Gene Manipulation* (1981), herein incorporated by reference, for a further discussion of cloning vehicles and gene manipulation procedures.

Alternatively, the process of purifying the protein, sequencing it and preparing oligonucleotide probes can be bypassed and direct observations of expression substituted instead. In this approach, a cDNA library is established as before by extracting cytoplasmic RNA from α chain expressing cells and is used to form complementary DNA as discussed above. The cDNA library cloned into *E. Coli* can then be incorporated into vectors with appropriate promoters (e.g., a Okyhama-Berg vector with an SV-40 promoter) and transfected in eukaryotic cells, such as African green monkey kidney cells (i.e., COS-7 cells), to express the α chain protein. Specific binding with radiolabeled IL-2 or radiolabeled monoclonal antibodies to an α chain epitope will permit the selection of functional transformants. To identify the bacterial colony containing the cRNA encoding the α chain, the bacteria are cloned and frozen. Pools of 10–20 bacterial colonies are then transfected into COS-7 cells, which are then assayed for α chain expression, either through IL-2 binding or by antibody binding. Positive pools are reassayed whereby each individual colony is transfected. After indentification of the positive bacterial clones, the cDNA insert can be handled as described above.

In another alternative approach to cloning, which is useful if the concentration of mRNA transcribing the α chain protein is low in a given cell, the total genomic DNA can be transfected into mouse fibroblasts. Mouse cells which express the surface receptor and can be identified, e.g., by rosette reaction with antibody-coated red blood cells. These mouse fibroblasts quantities can then be selected and used, according to steps described above, in constructing a cDNA library and isolating the gene of interest.

Diagnostic and Therapeutic Agents

The receptor proteins and reactive antibodies of the present invention can be used for a variety of diagnostic and therapeutic purposes. In a simple embodiment, soluble α chain proteins can be harvested from eukaryatic or prokaryotic cells (e.g., by following the protein purification steps described above) and used in both radiolabeled and unlabeled states in competitive binding assays to test for the presence of interleukin-2. Such assays can be valuable insofar as the binding affinity of α chain proteins for interleukin-2 appears to be higher than that typically reported for conventional anti-IL-2 antibodies. Similarly, monoclonal antibodies specific for the α chain protein (also prepared as described above) can be used in both radiolabeled and unlabeled states in competitive binding assays to detect the presence of the IL-2 receptor on cell samples. The α chain protein and antibodies can also be fixed to inert supports for assay purposes.

Various assay techniques can be practiced employing the reagents disclosed herein, including radioimmunoassays, enzyme immunoassays, heterogeneous and homogeneous assays, enzyme linked immunosorbent assays ("ELISA"), and the like. An exemplary assay for IL-2 employing α chain proteins can be carried out as follows: the sample (having an unknown concentration of IL-2 ) is first contacted with a known quantity of fixed α chain protein (or a portion of the protein containing the epitope) during which time IL-2 in the sample becomes bound to the α chain protein. The fixed support is then treated with a known quantity of radiolabeled IL-2 which binds to those sites on the fixed support which remain unoccupied. Excess label is then washed off, and the quantity of label remaining on the support is inversely proportional to the amount of IL-2 originally present in the sample.

An alternative assay for IL-2 can be constructed using the IL-2 receptor α chain fixed to a solid support (such as polystyrene beads or plastic microtiter wells). Samples containing IL-2 would be incubated with the α chain, allowed to bind, and then washed to remove any unbound IL-2. To detect the bound IL-2, a developing reagent consisting of monoclonal or polyclonal antibodies reactive with IL-2 that has been radiolabeled or enzyme-linked can be used. Alternatively, labeled IL-2 receptor β chain can also be employed since the binding sites on α and β chains interact with separate residues. See generally, Roitt, *Essential Immunology*, pp. 137–171 (Blackwell Press 1980) and U.S. Pat. No. 4,376,110 issued to David et al. on Mar. 8, 1983, incorporated by reference, for further descriptions of immunoassay techniques.

Fixation of α chain proteins to solid supports can also be useful as a means for (or additional step in) the purification of crude IL-2. For both assay and purification purposes, it may be useful to construct double affinity solid supports employing both the α and β chains, since these chains appear to recognize different portions of the IL-2 molecule and appear to exhibit synergistic affinity. Similarly, the fixation of monoclonal antibodies specific for the α chain protein can be used in purifying the receptor protein, as well as in recognizing and isolating cells expressing the protein.

Finally, the present invention can give rise to a number of therapeutic agents useful in treating various immune disorders. One class of such compounds includes antagonist compounds which would occupy the affinity sites on the T cells, blocking IL-2 reception and, thereby, serving as immunosuppressants. Such antagonist compounds can include the monoclonal antibodies (or active fragments thereof) specific for the α chain protein, itself, or portions of the protein (i.e. the extracellular domain) which include the IL-2 binding site. Such antagonist compounds can be particularly useful in combatting tissue and organ graft rejection in kidney, liver, heart and other transplants and so-called "graft versus host" disease in bone marrow transplants without the side effects associated with conventional immunosuppressants. The α chain receptor protein or fragments thereof containing the extracellular domain can also be useful as IL-2 sequestering agents which would remove IL-2 from the blood stream without effecting the T cells directly. Another class of therapeutic compounds includes agonist compounds which also react with the IL-2 α chain sites on T cells, thereby simulating IL-2 reception or perform functions analogous to those performed by IL-2 in stimulating T cell growth. Such compounds can consist of synthetic peptides identified and selected to bind to the α chain, or alternatively, monoclonal antibodies that bind to the same site normally occupied by IL-2.

The α chain protein can also be useful in designing highly specific drug deliver systems for T cells to treat immunodeficiencies, as well as abnormalities in which T cells express IL-2 receptors aberrantly such as in acute T cell leukemia, where the leukemic cells themselves continuously express high levels of IL-2 receptors. The α chain protein appears to be responsible, at least in part, for receptor-mediated endocytosis whereby IL-2 is internalized by T cells. This feature can be exploited to deliver metabolites, anti-metabolities, anti-viral agents and other therapeutic agents across the cytoplasmic membrane. In such instances, the therapeutic agent would be coupled to a synthetic (or genetically engineered) peptide that recognizes and specifically binds to the T cell affinity sites (i.e., the α chain alone or the α and β chains together), such that the conjugate becomes bound to, and ultimately absorbed by, the T cell.

I claim:

1. An interleukin-2 receptor protein, said protein having a specific affinity for interleukin-2 and characterized by having a molecular weight of about 75,000 (Mr) as determined by SDS/PAGE analysis under reducing condition and having an affinity for interleukin-2 of about $10^{-9}$ molar.

2. The protein of claim 1 wherein the protein is further characterized by
being substantially unreactive with anti-Tac antibodies.

3. The protein of claim 1 wherein the protein is further characterized as being derived from DNA encoding a surface protein on mammalian T cells.

4. The protein of claim 1 wherein the protein further comprises a labeling means for labeling the protein for use as a diagnostic reagent.

* * * * *